United States Patent [19]

Seidemann et al.

[11] Patent Number: 5,757,930
[45] Date of Patent: May 26, 1998

[54] APPARATUS AND METHOD FOR TESTING ATTENUATION OF IN-USE INSERT HEARING PROTECTORS

[75] Inventors: Michael F. Seidemann, Kenner; Roger P. Juneau, Destrehan; Juan H. Sanchez, Slidell, all of La.

[73] Assignee: Sound Tehcnologies, Inc., Kenner, La.

[21] Appl. No.: 338,846

[22] Filed: Nov. 14, 1994

[51] Int. Cl.⁶ ................................................. H04R 29/00
[52] U.S. Cl. ........................ 381/60; 381/68; 73/585; 128/866
[58] Field of Search ............................ 381/60, 68; 73/585; 128/746, 864, 865, 866, 867, 868

[56] References Cited

U.S. PATENT DOCUMENTS

| | | |
|---|---|---|
| 2,891,217 | 6/1959 | Grieg et al. . |
| 2,982,914 | 5/1961 | Stewart . |
| 3,202,931 | 8/1965 | Koontz, Jr. . |
| 3,217,247 | 11/1965 | Taber . |
| 3,631,346 | 12/1971 | Riggs . |
| 3,697,973 | 10/1972 | Stevens . |
| 3,729,598 | 4/1973 | Tegt . |
| 3,757,769 | 9/1973 | Arguimbau . |
| 3,906,158 | 9/1975 | Lake . |
| 3,968,334 | 7/1976 | Padilla . |
| 4,020,298 | 4/1977 | Epley . |
| 4,024,499 | 5/1977 | Bosscher . |
| 4,029,083 | 6/1977 | Baylor . |
| 4,060,701 | 11/1977 | Epley . |
| 4,061,041 | 12/1977 | Fletcher et al. . |
| 4,064,362 | 12/1977 | Williams . |
| 4,124,818 | 11/1978 | Lin et al. . |
| 4,374,526 | 2/1983 | Kemp ........................ 128/746 |
| 4,416,155 | 11/1983 | Kirby . |
| 4,477,770 | 10/1984 | Tojo . |
| 4,586,194 | 4/1986 | Kohashi . |
| 4,644,581 | 2/1987 | Sapiejewski . |
| 4,763,753 | 8/1988 | Killion . |
| 4,781,196 | 11/1988 | Killion . |
| 4,813,430 | 3/1989 | Hecox . |
| 4,852,683 | 8/1989 | Killion . |
| 4,966,160 | 10/1990 | Birck . |
| 5,044,373 | 9/1991 | Northeved . |
| 5,113,967 | 5/1992 | Killion . |
| 5,317,273 | 5/1994 | Hanson ........................ 381/58 |

FOREIGN PATENT DOCUMENTS 94022372  10/1994  WIPO ........................ 128/746

Primary Examiner—Curtis Kuntz
Assistant Examiner—Minsun Oh
Attorney, Agent, or Firm—Pravel, Hewitt, Kimball & Krieger

[57] ABSTRACT

The device of the present invention is designed for the purpose of providing a system for conducting objective assessment of the actual or "real world" attenuation which is provided by insert-type hearing protection (IHP) devices. The device is constructed to serve as the input device to any commercially available noise dosimetry instrument or sound level measuring device. A miniature microphone is mounted on, or embedded in the proximal surface of the IHP which is to be inserted in the ear or upon the ear of the user. The miniature microphone is hard wired to a miniature jack which is mounted on, or embedded in the distal surface of the IHP device. A cable connects to the jack on the outside of the IHP device and to the input of the noise dosimetry instrument or sound level measurement device. Thereby, when the IHP device containing the above is used, the dosimetry or sound level measurement instrument conducts assessments of actual sound levels to which the hearing mechanism is exposed when IHP devices are in use. In that manner, objective assessment of IHP device effectiveness is accomplished, allowing the ability to obtain experienced (laboratory) vs. non-experienced (real world) data. Furthermore, inter-subject and intra-subject variability as well as intra-IHP and inter-IHP variability data can be collected with the use of this device and method. This device and method also eliminate the need for any audiometric equipment necessary for the prior art assessment of the effectiveness of IHPs in general.

11 Claims, 3 Drawing Sheets

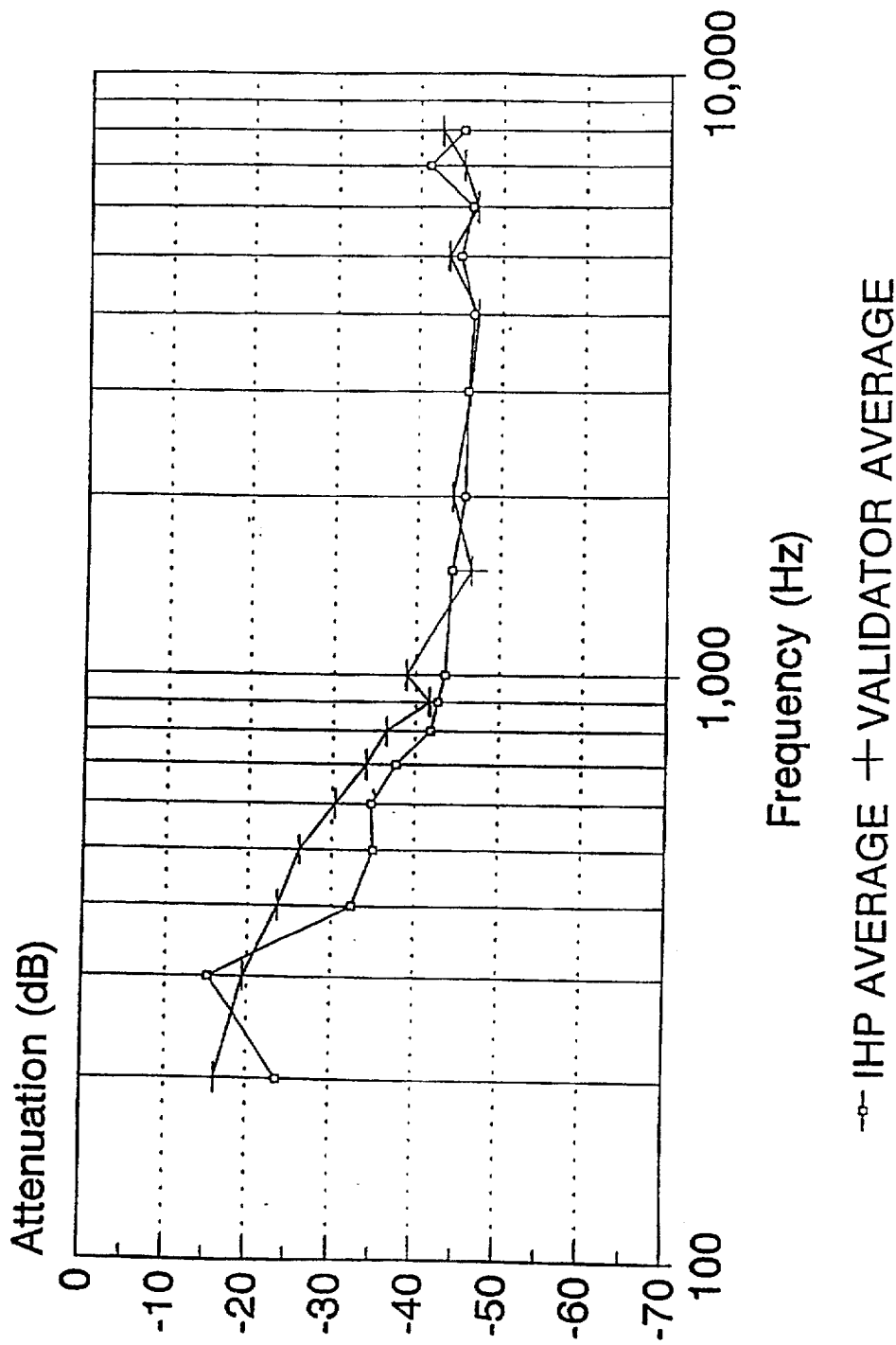

APPARATUS AND METHOD FOR TESTING ATTENUATION OF IN-USE INSERT HEARING PROTECTORS

BACKGROUND OF THE INVENTION

Approximately nine million workers in the United States are exposed to potentially hazardous noise levels in the workplace.

Federal regulation of occupational noise exposure levels (OSHA: CFR 1910.95) has been in place for more than a decade. That regulation provides for use of hearing protection devices in numerous instances of exposure to potentially hazardous levels of workplace noise in order to prevent occupational noise-induced hearing loss. Manufacturers of hearing protection devices are required to label products in terms of noise reduction capability according to the procedures promulgated by the Environmental Protection Agency. That specification is designated as the Noise Reduction Rating (NRR). The method used to calculate the NRR is a laboratory procedure. For more than ten years, scientific research has extensively and consistently demonstrated that the NRR in no way accurately represents the actual, "real world" attenuation of workplace noise which is provided by hearing protection devices. Numerous variables, such as individual fit, insertion or application technique, training, etc., affect the "real world" attenuation provided by hearing protectors. As a result, several computational procedures have been proposed in the scientific literature (such as derating the NRR by 7 dB or by 50%) in an attempt to render a modification of the NRR a more realistic estimate of the actual protection provided. However, all such techniques remain computational, and do not provide a means of objectively measuring the actual level of workplace noise which penetrates the hearing protection device and reaches the worker's hearing mechanism, possibly causing irreversible hearing loss.

Such objective measurement will provide employers with the ability to assess in-situ the actual levels of noise sustained by employees, and thereby, a mechanism to more realistically reduce or prevent occupational noise-induced hearing loss. In turn, the reduction of the incidence of occupational noise-induced hearing loss will reduce the number of compensation claims filed against employers for such impairments, and thereby should reduce the cost of worker's compensation insurance. Ultimately, such cost containment associated with production should reduce consumer costs of products.

SUMMARY OF THE INVENTION

An inexpensive input device and method is provided for in-situ testing and objective measurement of the noise reduction provided by hearing protection devices. This invention serves as an input device to standard, commercially available sound measuring instruments (sound level meters and noise dosimeters).

The apparatus consists of a miniature microphone mounted on the end of a hearing protector which is closest to the wearer's eardrum. The miniature microphone is connected to a jack on the outside surface of the hearing protection device. A cable is used which plugs into the jack on the hearing protection device on one end, and terminates in a signal conditioning stage and plug on the opposite end. The terminal plug connects to a commercially available sound level meter or noise dosimeter.

The device is to be used in the workplace while performing actual daily work operations. By using the device for a representative period of work time, employers will readily be able to assess the adequacy, fit, usage, and effectiveness of the hearing protection device, as well as providing documentation of compliance with federal and state statutes which require not only the mere application of hearing protection devices, but also an assessment of their adequacy relative to the prevention of occupational noise-induced hearing loss.

The use of this device significantly expands the scope of measurement of sound level meters and noise dosimeters. Those instruments until now have been able to assess ambient sound conditions in the absence of the use of hearing protection devices. This invention enables sound level meters and noise dosimeters to measure the effect of hearing protection devices upon the ambient noise environmental conditions.

The present invention comprises a device for measuring noise level from the proximal end of an insert-type hearing protector (IHP) placed in the user's ear canal comprising:

a commercially available IHP;

a microphone placed at the proximal tip of the hearing protector for transmitting sound from within the airspace between the proximal tip of the IHP and the tympanic membrane;

a connector at the distal end of the IHP for mechanically and electrically coupling the microphone/IHP assembly to the cable assembly;

a cable assembly for electronically coupling the microphone to a noise dosimeter or other sound measuring apparatus comprising an amplifier and/or an impedance matching network; and a connector for mechanically and electrically coupling the cable to the noise dosimeter or other sound measuring apparatus.

The present invention also comprises an objective method for measuring the sound attenuating effectiveness of IHPs in general in any environment, comprising the steps of:

calibrating the dosimeter in the same manner as it would be if using the regular microphone but instead using the device of the present invention;

using the device of the present invention to measure the noise level within the ear canal; and measuring the output transmitted by the device of the present invention using a noise dosimeter or other sound measuring apparatus, allowing the experimenter to obtain various noise dose measurements such as time weighted average and peak levels, among others.

The method of the present invention provides the employee and employer with a means of selecting the appropriate type and size of IHP to be worn by an employee at the worksite, based on fit and IHP performance in the employee's ear.

The method of the present invention can be used by the governments of the United States and other countries and municipalities for qualifying and quantifying the amount of protection that an IHP can provide to employees at their respective worksites.

The method of the present invention provides the experimenter with a portable means of testing several IHPs at different locations within a worksite.

With the method of the present invention, manufacturers of IHPs can test the effectiveness of new and existing IHPs on a pre-determined number of users in order to obtain a better estimate of the IHP's ideal NRR, as well as the "real world" NRR.

The method of the present invention can be used with various sound sources including pure tones, pink noise, and worksite ambient noise, among others.

The method of the present invention can provide a means of objectively qualifying and quantifying an employee's ability to use a particular IHP, when it includes the additional steps of:

the employee inserting the device of the present invention as he usually wears the IHP;

the device being connected to the noise dosimeter, the employee being exposed to the noise environment needed for the test;

the amount of protection provided by the IHP as inserted by the employee being compared to the manufacturer determined NRR rating of the IHP and by comparison it can be determined whether or not the employee is wearing the IHP in an effective manner, and whether or not the employee needs further training in the proper use and insertion of the IHP or whether a more appropriate type or size of IHP should be recommended.

The method of the present invention can be used in legal investigations to better understand the cause of an employee's hearing loss by determining whether a hearing loss could have occurred due to an IHP's inability to provide the necessary protection or the employee's inability to properly use the IHP.

STATEMENT OF THE OBJECTS OF THE INVENTION

A principal object of this invention is to make use of existing (and hereon future) technology embodied in various forms of sound measurement devices (noise dosimeters and sound level meters) while providing an innovative input device to be used in conjunction with sound measurement devices in order to yield an objective assessment of the "real world" effectiveness of hearing protection devices.

Another important object is to enable the conduction of such measurements in realistic workplace locations rather than in a laboratory.

Still another object is to provide industries and governments with a means to assess the effectiveness of hearing protection programs so that the prevalence of occupational noise-induced hearing loss may be reduced.

Other objects, advantages, and novel features of the invention will become apparent from the following detailed description of the invention when considered in conjunction with the accompanying drawings.

BRIEF DESCRIPTION OF THE DRAWINGS

FIG. 4 shows the attenuation characteristics of the device or modified hearing protector, as well as the intact hearing protector.

DESCRIPTION OF THE PREFERRED EMBODIMENT

Figure 1:
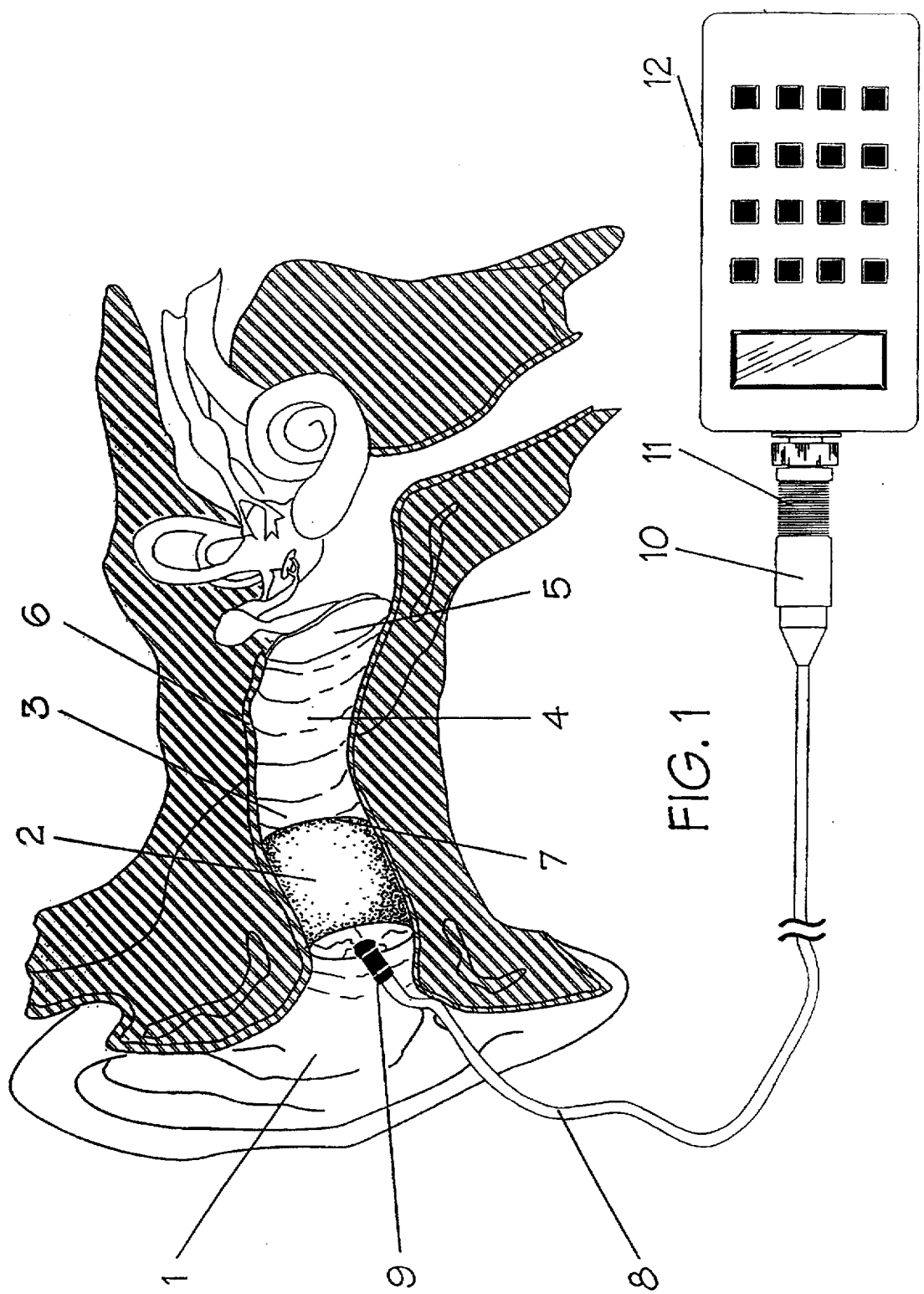
FIG. 1 shows the device as it would be worn in the ear.

The device of this invention is meant to be inserted in the human ear which is marked as 1 in FIG. 1. The modified hearing protector is depicted as 2. The microphone 3 (hidden in picture) measures the noise level to which the volume of air 4 (defined by the tympanic membrane 5, the canal wall 6, and the proximal end of the hearing protector 7) is exposed. The sound in said air space is converted (transduced) into an electrical signal by the microphone 3, and directed to the cable assembly through a mini-plug 9. The signal travels through the cable and is modified by a signal conditioning network 10 so it can be coupled through the connector 11 to the noise dosimeter or other sound level measurement equipment 12. The modified hearing protector 2 would be inserted into the ear 1 exactly in the same manner as the intact hearing protector would, according to the hearing protector manufacturer's instructions.

Figure 2:
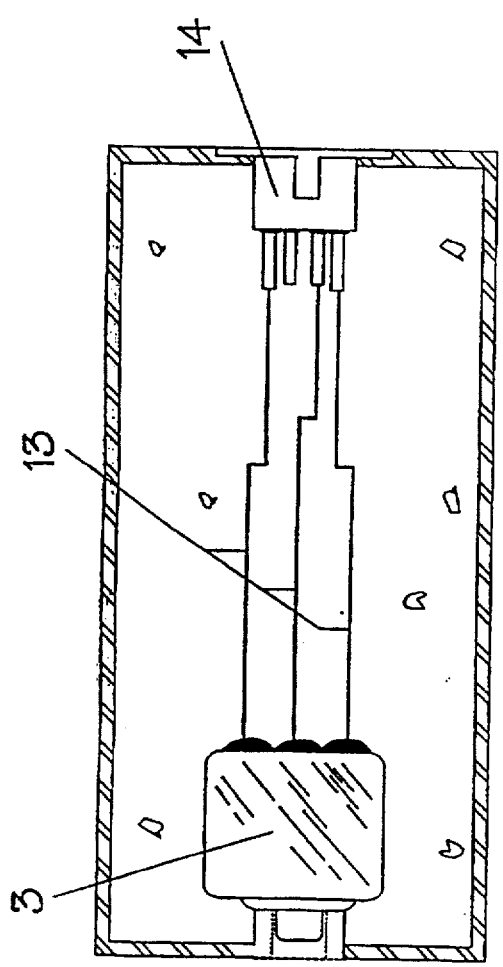
FIG. 2 is a longitudinal cross-sectional view of the modified hearing protector, showing the microphone and mini-plug embedded in the hearing protector.

A cross-sectional view of the hearing protector assembly is shown in FIG. 2. The microphone 3 is embedded in the side 7 of the hearing protector 2 which is inserted first into the ear 1. Wires 13 connect the microphone 3 to one side of the mini-connector system 14. As can be seen in FIGS. 1 and 2, hearing protector 2 is a generally cylindrical plug.

Figure 3:
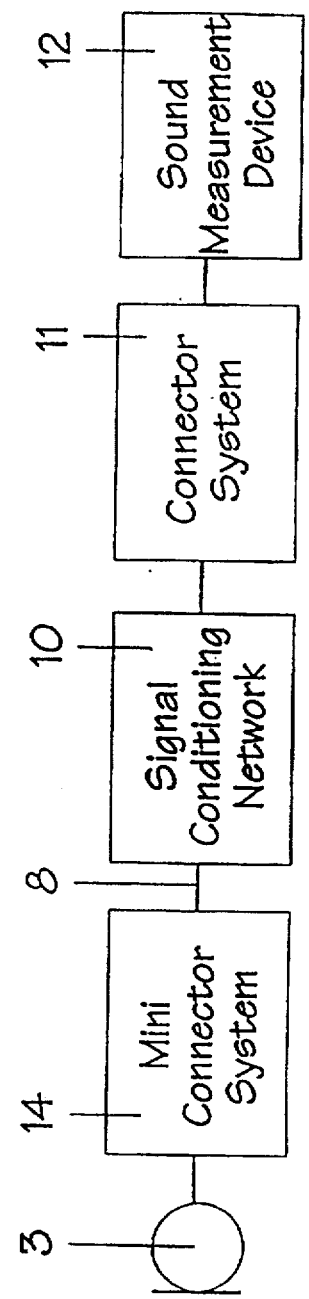
FIG. 3 is a block diagram depicting the electrical relationship between the different components, including the microphone, mini-plug assembly, signal conditioning network, and connector to a sound level measuring device.

The complete system is depicted in FIG. 3. The sound enters the microphone 3 and is directed to one side of the mini-connector system 14. The microphone 3 and half of the mini-connector system 14 are embedded in the distal end of hearing protector 2 (not shown in FIG. 3). The electrical signal then travels through a cable 8 to the signal conditioning network 10 (comprising an amplifier and/or an impedance matching network). This signal conditioning network 10 can be comprised of active or passive components such as an amplifier, filters, and other discrete components, in order to appropriately couple the signal to the sound level measuring device 12. The signal conditioning network 10 is coupled to the sound level measuring device 12 through a connector system 11 that matches the one used by the sound level measuring device.

In order to avoid changing the hearing protector's attenuation characteristics, minimum size cavities are made into the hearing protector in order to accommodate the microphone 3 and half of the mini-connector system. FIG. 4 shows the attenuation characteristics of the intact and modified hearing protectors. As can be seen in FIG. 4, the IHPs attenuate between about 15 dB and 45 dB of the noise level of a 90 dB input signal. The data is the average for nine intact hearing protectors ("IHP Average") and the average of nine modified hearing protectors ("Validator Average"). Different hearing protectors were considered with similar NRR ratings. The modifications show that the attenuation of low frequencies (<500 Hz) is reduced by 10 dB, reduced by 5 dB between 500 and 1,000 Hz, and remains unaffected for higher frequencies (>1 kHz). A study will be published in the near future to assess whether or not the differences for the low and mid frequencies are statistically significant and whether or not they affect the accurate measurement of noise levels.

What is claimed is:

1. A device for measuring noise level from a proximal tip of an insert-type hearing protector (IHP) placed in a user's ear canal, the user having a tympanic membrane, wherein the proximal tip of the IHP faces the user's tympanic membrane and the IHP has a distal tip, and there is an airspace between the proximal tip of the IHP and the tympanic membrane, the device comprising:

a. an IHP which can attenuate between about 15 dB and 45 dB of the noise level reaching the distal tip of the IHP;

b. a microphone placed at the proximal tip of the IHP for transmitting sound from within the airspace between the proximal tip of the IHP and the tympanic membrane;

c. electronic coupling means for electronically coupling the microphone to a sound measuring means.

2. An objective method of measuring the sound attenuating effectiveness of an insert-type hearing protector (IHP), comprising the steps of:

a) providing a device for measuring noise level from a proximal tip of an IHP placed in a user's ear canal, the user having a tympanic membrane, wherein the proximal tip of the IHP faces the user's tympanic membrane and the IHP has a distal tip, and there is an airspace between the proximal tip of the IHP and the tympanic membrane, the device comprising:

(i) an IHP which can attenuate between about 15 dB and 45 dB of the noise level reaching the distal tip of the IHP;

(ii) a microphone placed at the proximal tip of the IHP for transmitting sound from within the airspace between the proximal tip of the IHP and the tympanic membrane; and (iii) electronic coupling means for electronically coupling the microphone to a sound measuring means;

b) calibrating the sound measuring means using the microphone; and c) using the device to measure noise level within the ear canal of the user, the ear canal having the IHP placed therein.

3. The method of claim 2, further comprising the step of selecting an appropriate type and size of IHP to be worn by an employee at the worksite, based on fit and IHP performance in the employee's ear.

4. The method of claim 2, further comprising the step of qualifying and quantifying the amount of protection that an IHP can provide to employees at their respective worksites.

5. The method of claim 2, further comprising the step of testing the effectiveness of an IHP on a pre-determined number of users in order to obtain a better estimate of the IHP's ideal NRR, as well as the "real world" NRR.

6. The method of claim 2, wherein pure tones are used as a sound source.

7. The method of claim 2 wherein such method provides a means of objectively qualifying and quantifying an employee's ability to use a particular IHP, comprising the additional steps of:

a. the employee inserting the IHP as he usually wears an IHP for hearing protection;

b. the employee being exposed to the noise environment needed for the test;

c. the amount of protection provided by the IHP as inserted by the employee being compared to the manufacturer determined NRR rating of the IHP and by comparison it can be determined whether or not the employee is wearing the IHP in an effective manner to attenuate noise, and whether or not the employee needs further training in the proper use and insertion of the IHP or whether a more appropriate type or size of IHP should be recommended.

8. The method of claim 2, wherein pink noise is used as a sound source.

9. The method of claim 2, wherein worksite ambient noise is used as a sound source.

10. The device of claim 1, wherein the sound measuring means comprises a dosimeter.

11. The device of claim 1, wherein the electronic coupling means includes:

a cable assembly and a connector, the connector being at the distal tip of the IHP for mechanically and electrically coupling the microphone to the cable assembly, the cable assembly electronically coupling the connector to the sound measuring means.

* * * * *